(12) United States Patent
Nidetzky

(10) Patent No.: US 6,306,160 B1
(45) Date of Patent: *Oct. 23, 2001

(54) SOFT LASER WITH AN INTEGRATED POINT FINDER FOR ACUPUNCTURE POINTS

(75) Inventor: J. Leopold Nidetzky, Vienna (AT)

(73) Assignee: Myles Limited, Douglal (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/587,617

(22) Filed: Jan. 17, 1996

(30) Foreign Application Priority Data

Jan. 17, 1995 (AT) .......................................... 59/95

(51) Int. Cl.⁷ ................................................... A61N 21/00
(52) U.S. Cl. ........................... 607/89; 600/548; 128/907; 606/2; 606/13; 606/42
(58) Field of Search ................................... 128/735, 907; 607/88, 89; 606/2, 13, 42, 9; 600/548

(56) References Cited

U.S. PATENT DOCUMENTS

| | | | |
|---|---|---|---|
| 4,232,678 | * 11/1980 | Skovajsa ............................... | 128/907 |
| 4,535,784 | * 8/1985 | Rohlicek et al. ...................... | 128/735 |
| 4,694,840 | * 9/1987 | Kairis et al. .......................... | 128/735 |
| 4,940,060 | * 7/1990 | Gu et al. ............................... | 128/907 |
| 5,250,068 | * 10/1993 | Ideguchi et al. ...................... | 128/907 |
| 5,358,503 | * 10/1994 | Bertwell et al. ....................... | 606/27 |
| 5,409,482 | * 4/1995 | Diamantopoulos .................... | 607/89 |

FOREIGN PATENT DOCUMENTS

| | | | |
|---|---|---|---|
| 2703927 | * 8/1978 | (DE) | ..................................... 128/735 |
| 0 079 615 | 5/1983 | (EP) | ............................... A61N/5/00 |
| 0079615 | 5/1983 | (EP) | ............................... A61N/5/00 |
| 416150 | * 3/1991 | (EP) | ....................................... 607/89 |
| 0 437 636 | 7/1991 | (EP) | ............................. A61H/39/00 |
| 0 465 459 | 1/1992 | (EP) | ............................. A61H/39/00 |
| WO 95/03089 | 2/1995 | (WO) | ............................. A61N/5/02 |

\* cited by examiner

*Primary Examiner*—John P. Lacyk
*Assistant Examiner*—Rosiland Kearney
(74) *Attorney, Agent, or Firm*—Karl Hormann

(57) ABSTRACT

A soft laser unit is described with a housing and a skin resistance measuring device for localizing acupuncture points which contains a probe electrode, a measuring circuit connected therewith and a display device connected to the latter. The unit additionally contains a biostimulation or therapy laser unit, in particular for laser acupuncture, and an exit opening for the laser beam of the laser unit with a focusing optic is provided within the probe electrode, whereby in the state mounted on the patient's skin the laser beam focus of the laser unit comes to lie generally in the plane of the face of the probe electrode, i.e. on the skin surface.

The soft laser unit can also be utilized in continuous operation as a so-called "laser shower", without touching the skin, by fixing the probe electrode in the pressed-in state.

16 Claims, 2 Drawing Sheets

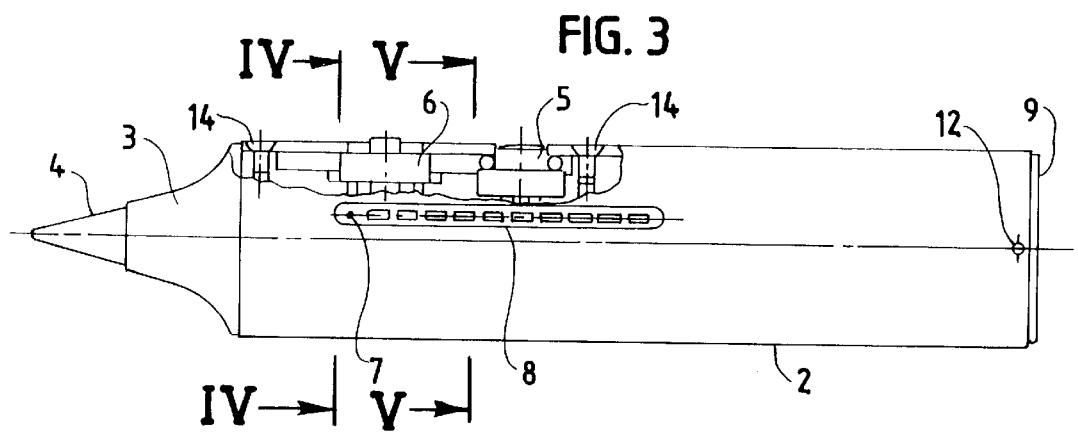
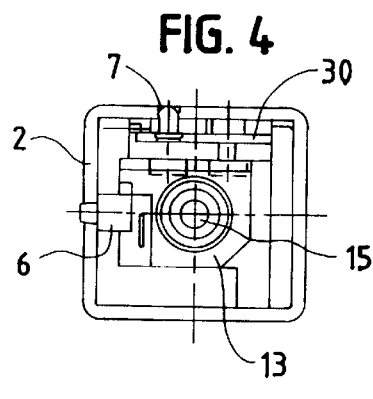
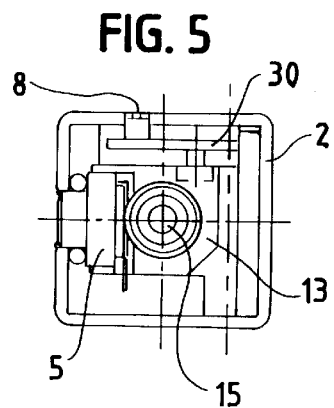
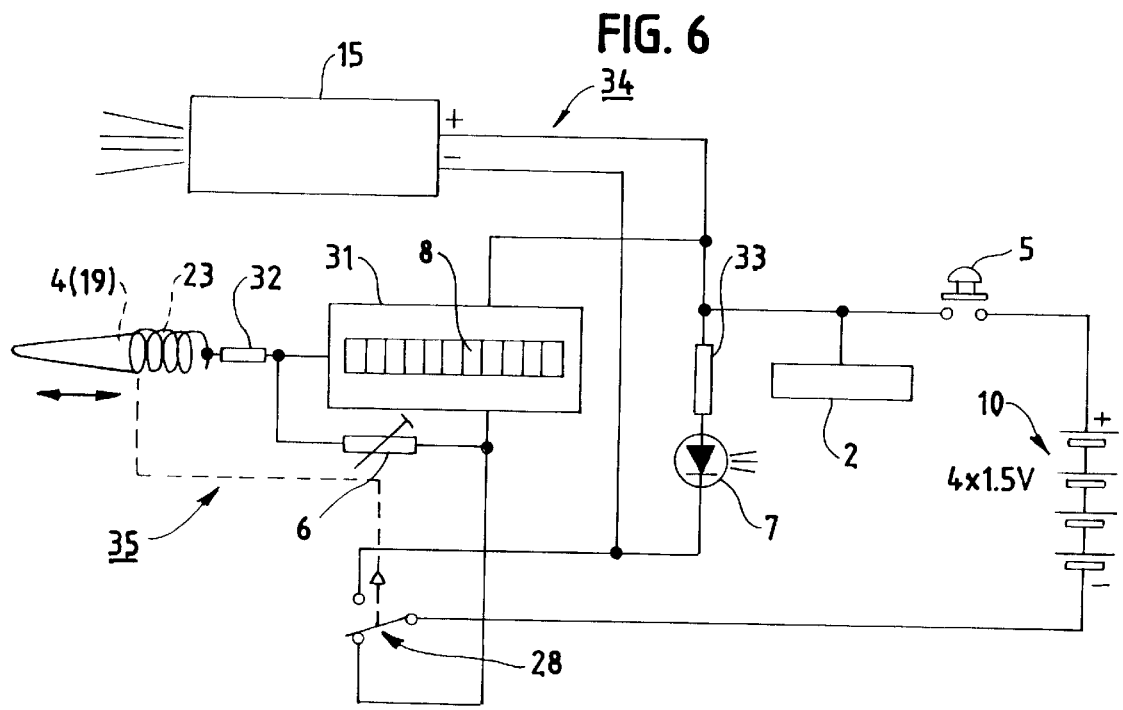

SOFT LASER WITH AN INTEGRATED POINT FINDER FOR ACUPUNCTURE POINTS

FIELD OF THE INVENTION

This invention relates to a soft laser unit for biostimulation and acupuncture with an integrated point finder for localizing acupuncture points, said unit containing a probe electrode generally point-shaped in projection, a measuring circuit connected therewith and an optical display device connected to the latter.

BACKGROUND OF THE INVENTION

DE-B-2 602 519 discloses a device for locating acupuncture points which is based on the principle of skin resistance measurement, acupuncture points being detected when the skin resistance value drops considerably. To permit the acupuncture points to be reliably defined, this known device is provided with self-adjusting means for the display so as to lay the display in the optimum display range with respect to the patient depending on his skin quality, for example dry or moist skin.

A similar device for localizing acupuncture points is disclosed in DE-C-3 048 358, where two coaxially nested, elastically interconnected and displaceable test electrodes are provided for indicating, in accordance with the position of the electrodes, whether gold needles or silver needles should be used for the acupuncture.

In the abovementioned devices, as in the device according to CH-A-573 747, it is disadvantageous that for performing the actual acupuncture the device with which the acupuncture points have been localized must be lifted off the localized points and the puncture then performed with needles in the conventional way. It is difficult to insert the needles at exactly the sites determined as acupuncture points since when the probe is removed the site of the determined acupuncture points can only be marked approximately. On the other hand the acupuncture points must be kept to with a precision of ½ mm or 1 mm if acupuncture is to be effective.

Further, it is known from EP-A-416 150 to use a laser unit with a diode laser unit for biostimulation of organic tissue, the laser beam being used for performing laser acupuncture or else a so-called laser shower for treating the area of a skin site with the laser beam, for example in the treatment of herpes simplex. With this laser unit formed as a hand-held device the laser beam emerges on one face through an opening within a sensor ring, it being possible to switch on the device only if this sensor ring is in contact with the patient's skin. In the case of laser acupuncture there is the difficulty of previously localizing the acupuncture points, marking them and then making the laser unit act at exactly these acupuncture points.

EP 0 495 757 A1 describes a treatment pin with which the acupuncture points are localized as usual by measuring skin resistance, the display being preferably realized by an LED band, and with which treatment takes place subsequently, without having to lift off the ring-shaped point finder, by switching on an electric power surge or alternatively by switching on a laser beam, the laser beam being produced by a laser diode and conducted awkwardly by a coaxial light guide which absorbs considerable laser energy during coupling-in and decoupling and moreover does not hit in focus. The light energy available on the skin surface is accordingly attenuated by the beam conduction by light guide, so that if a laser of laser protective class 3a (3 mW power) is used and there is no focusing on the skin surface the stimulating effect on the acupuncture point is insufficient in many cases.

However it is preferable to use a diode laser of protective class 3a since no expensive precautions are necessary for operating such lasers. This fact is especially important when the unit is designed as a hand-held device and to be used by the patient himself, who should be able to handle the unit easily and with no problem after being given basic instructions by the doctor.

The laser beam should cause optimum stimulation of the acupuncture point and also be applicable successfully for biostimulation, for example for treating herpes simplex or individual acne points.

BRIEF SUMMARY OF THE INVENTION

These problems are solved if the inventive unit contains a biostimulation or therapy laser unit known in the art which is additionally suitable in particular for laser acupuncture, the laser beam being produced by a semiconductor laser with a wavelength of preferably 635 to 670 nm (nanometers), being focused by a corresponding optic, the focus coming to lie exactly on the skin surface due to suitable measures upon use as an acupuncture laser, the laser belonging to the category of laser protective class 3a, and the integrated point finder, which displays the localized acupuncture point by maximum length of a luminous bar, being switchable to the ranges dry, normal and moist skin to guarantee maximum reliability in the display for the particular case.

The present unit thus combines the function of acupuncture point localization with that of acupuncture treatment itself, with the help of a laser beam, whereby the unit does not have to be lifted off the particular acupuncture point between these two processes. Acupuncture treatment can therefore take place exactly at the site which was previously localized precisely as an acupuncture point, it also being of importance that the laser beam emerges directly through an opening in the probe electrode and the focus of the laser beam lies in the plane of this probe electrode, which is still in contact with the user's skin.

The unit can be designed as a self-contained hand-held device in the manner of a stylus with a built-in battery power supply and thus with no cable connection. The probe electrode further preferably forms a test prod for the skin resistance measurement, whereby the diameter can be small enough—at least on the face in contact with the skin—to permit acupuncture points to be localized with the necessary precision.

The unit is thus especially suitable for painless self-help in case of pain or diseases which respond to acupuncture treatment,and it is also of advantage that there is no risk of infection since no acupuncture needles are inserted in the skin. In comparison with electroacupuncture it is of advantage that there is no unpleasant electric shock, apart from the medically proven fact that excessive load on an acupuncture point by electric current leads to desensitization of the acupuncture point in question.

For reasons of production engineering as well as safety reasons it is of advantage if the laser unit is formed by a diode laser known in the art, preferably with a wavelength of 635 to 670 nm (nanometers). Such a diode laser is commercially available as a small handy unit which ensures an optimal effect for acupuncture in particular at the stated wavelength of 635 nm, since studies have shown that the penetration depth in skin or body tissue is especially great at this wavelength, that is to say, greater than for radiation of a different wavelength. The output of the diode laser can be limited advantageously to 3 mW (milliwatts) so that the laser falls within laser class 3a, i.e. is classified as fully harmless, so that no additional precautions are necessary.

A further safety function is to be seen in the fact that the laser beam diverges greatly directly after emerging from the unit, for which purpose the laser unit is preferably equipped with a short focal length optic. With such an arrangement the laser beam already fans out so far at a very short distance from the exit opening that the power per surface unit is low enough not to endanger the eyes, for example, should the laser beam be aimed directly into the eyes.

Relatively brief action of the laser unit is normally required for laser acupuncture, whereas longer-lasting operation of the laser unit, for example over several minutes, is desirable for other applications, for stimulation or therapy of organic tissue (including the so-called "laser shower"). To allow for both these functions easily, it is therefore of advantage if the laser unit has associated therewith a switching device for touch-key operation or continuous operation alternatively.

An especially advantageous embodiment of the inventive unit is characterized in that the probe electrode is formed by a hollow member, as known in the art, said hollow member being mounted in the housing in elastically movable fashion between an inoperative position and an operative position shifted inward into the housing, the hollow member having associated therewith a switch for the laser unit operable in the inward shifted operative position. In this embodiment the elastically movable hollow member forming the probe electrode serves at the same time to operate the switch for switching on the laser unit, so that after localization of an acupuncture point on the user's skin, which already involves an elastic inward shift of the hollow member, the laser unit is activated to emit the laser beam by stronger pressing-in of the hollow member. To switch off the skin resistance measuring device simultaneously, the switch is advantageously designed as a reversing switch. When the unit is lifted off the skin area and the hollow member thus moved back due to the spring force, the switch is restored so that the laser unit is switched off.

The elastically movable hollow member further furnishes the advantage that the—relatively small—spring force obtains a standardization in the contact pressure of the hollow member on the particular skin site; the contact pressure corresponds generally to the spring force. This consequently obtains a standardization for the skin resistance measurement.

An additional operating switch for the laser unit is advantageously provided for safety reasons electrically in series with the switch operable by the hollow member, so that both stronger pressing-in of the hollow member and operation of the operating switch are necessary for switching on the laser unit. In this connection it is further favorable if the operating switch is designed for touch-key operation, i.e. provided as a pushbutton switch, so that the laser unit can only be activated if this operating switch is held down against a spring force. As soon as the finger or thumb is taken from the operating switch the latter returns to its off-condition, thereby in any case making the laser unit dead. This also has the advantage that unintentional operation of the laser unit is always avoided when the unit is laid aside.

To permit the abovementioned continuous operation of the laser unit, it may be expedient in the embodiment with the probe electrode hollow member not to provide a separate continuous-operation switch but instead to use the hollow member itself for continuously switching on the laser unit. It is thus especially favorable if the hollow member has associated therewith a catch for locking it in the operative position.

To permit the hollow member to be easily locked in its completely pushed-back position, it is further advantageous if the catch is formed by a lockable spring catch whose catch pin is adapted to be brought into releasable engagement with the hollow member. Such lockable spring catches are known in the art for a great variety of applications and available as units, so that closer explanation here is unnecessary.

It is further of particular advantage here if the hollow member has a slot recess for engaging the catch pin, and a guide pin fixed on the housing protrudes into this slot recess for guiding the hollow member in its reciprocating motion between the inoperative position and the operative position.

It has also proven advantageous if the switch has associated therewith for its operation an elastically movable, e.g. lamellar switch lever in engagement with the hollow member. The lamellar, elastic switch lever can for example likewise engage a longitudinal slot in the hollow member so that it serves at the same time to guide the latter longitudinally, and when the hollow member is pushed back completely the switch lever comes to stop at the end of the longitudinal slot, then being pushed back against its spring force to operate the switch by the hollow member upon further insertion of the latter.

For the various functions of the probe electrode hollow member it is especially favorable if the hollow member has a generally conical, hollow test prod adjoining the front of a cylindrical hollow bearing portion, the face of said test prod forming a ring-shaped contact surface for the skin resistance measurement. The contact surface can be extremely narrow, with a diameter in the range of 1 mm or less.

With regard to the skin resistance measuring function it is often also favorable if the hollow member is made of brass and the housing forming the counterelectrode is an aluminum extruded section member. This simultaneously ensures low-priced production.

BRIEF DESCRIPTION OF THE DRAWINGS

The invention will be explained further in the following with reference to an embodiment illustrated in the drawing.

The drawing shows specifically:

FIG. 3 a partly broken open view of the unit in a position turned 90° from the representation in FIG. 2;

FIG. 4 a schematic sectional view substantially according to line IV—IV in FIG. 3;

FIG. 5 a further schematic sectional view substantially according to line V—V in FIG. 3; and FIG. 6 an electric circuit diagram of the unit.

DETAILED DESCRIPTION

Figure 1:
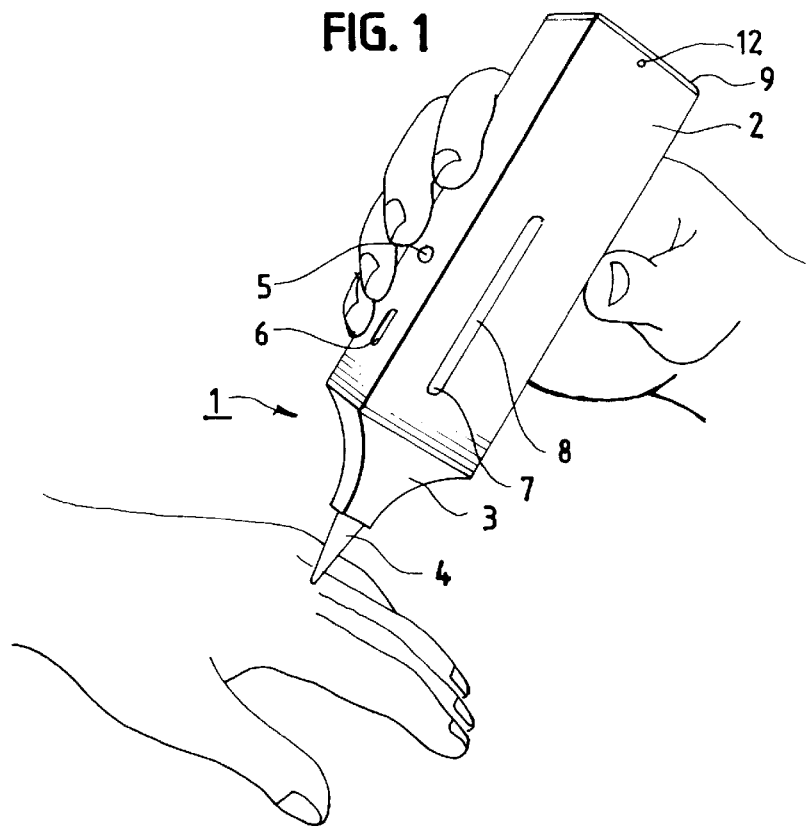
FIG. 1 a combined acupuncture point localizing and laser acupuncture unit in a graphic representation during application.

FIG. 1 illustrates, in use, a unit generally designated as 1 both for locating acupuncture points and for laser acupuncture, unit 1 being designed generally in the manner of a self-contained hand-held stylus, having elongate housing 2 for example with a square cross section and consisting e.g. of an aluminum extruded section which is aluminum-coated or provided with a different conductive coating layer at least in certain areas, and continuing at its front end into tapered, approximately prismatic plastic bearing member 3 which provides longitudinally slidable mounting of spring-loaded, electroconductive test prod 4, whose design and function will be explained more closely in the following with reference to FIGS. 2 to 5.

Figure 2:
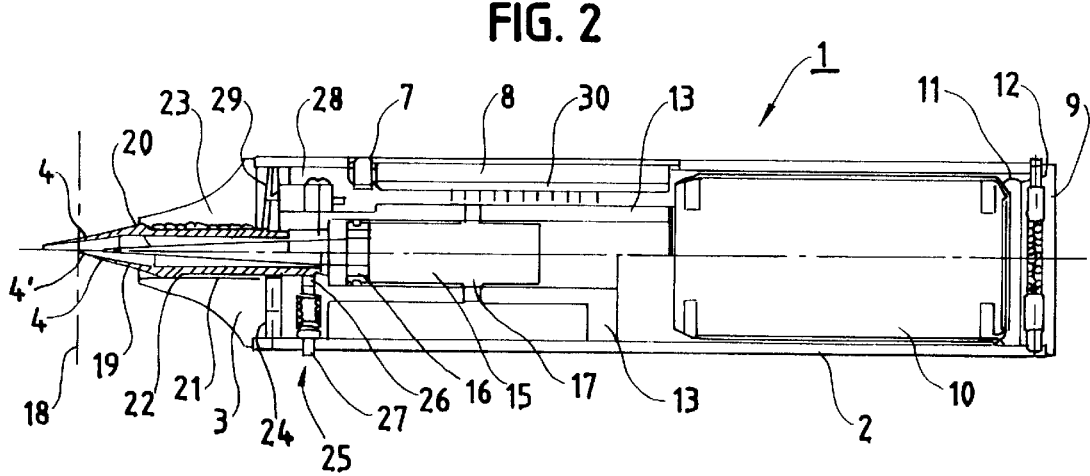
FIG. 2 a longitudinal section through this unit, the probe electrode formed by a hollow member being illustrated in the pushed-out inoperative position in the upper half of the representation and in the pushed-in operative position in the lower half of the drawing.

Unit 1 is equipped with operating switch 5 protruding outward through housing 2 and with sensitivity slide switch 6, e.g. with three positions in accordance with three sensitivity ranges for different skin resistances, and for purposes of display laser pilot lamp 7 and optical display device 8 formed by a row of light-emitting diodes are further provided; at the back end housing 2 of unit 1 is closed by cover 9, cover 9 being for example snapped in housing 2 and closing a battery compartment with battery block 10 (see FIG. 2). According to FIG. 2 cover 9 is equipped with springloaded locking or catch pin 11 which snaps into corresponding housing bore 12 when cover 9 is snapped onto the end of the housing.

Bearing member 3 prolonging the front of housing 2 is for example part of plastic mounting body 13 which carries various electric and mechanical components of unit 1 in the interior of housing 2. Mounting body 13 can for example be inserted into housing 2 from the front and fixed therein with the help of screws 14 (see FIG. 3). It should be noted that mounting body 13 is only apparent schematically and partly in FIGS. 2, 4 and 5, but the representations in FIGS. 2 to 5 clearly indicate the mutual association and arrangement of the individual components to be explained more closely in the following, thereby also indicating the specific design of mounting body 13 to the expert.

Diode laser unit 15 with lens 16 is disposed in the interior of mounting body 13, whereby adjusting screws 17 inserted in bores in mounting body 13 permit exact axial adjustment of diode laser 15. In operation, when test prod 4 is pressed in (see the representation in the lower half of FIG. 2), diode laser unit 15 emits a laser beam passing through the tapered interior of probe electrode conically hollow member 19 and focused by lens 16 at a plane 18 coinciding with the exit opening 4' on the face of test prod 4. The laser beam is indicated in FIG. 2 at 20.

This probe electrode is hollow member 19 whose front portion is conical and forms abovementioned test prod 4 which protrudes out of housing 2 or bearing member 3 and is generally point-shaped or—because of exit opening 4'—generally ring-shaped in a front view, with a small diameter (in the range of 1 mm or less), conical test prod 4 being adjoined at the back end by tubular bearing portion 21 via shoulder 22. Lying against shoulder or projection 22 is coil spring 23 which is supported with its other end on a radially inward protruding flangelike projection of bearing member 3 not specified in the drawing, so that hollow member 19 can be shifted axially inward against the spring force of coil spring 23, as indicated schematically in FIG. 2 by the different positions of hollow member 19 in the upper and lower halves of the drawing.

In its back end area, tubular or sheath-shaped bearing portion 21 has two diametrically opposite longitudinal slots not specified in the drawing, into one of which guide and stop pin 24 protrudes, on the one hand forming a protection against torsion for hollow member 19 and guiding the springloaded longitudinal motion thereof, and on the other hand serving as a stop for limiting the inward motion of hollow member 19 against the force of spring 23. The longitudinal slot which guide pin 24 engages is disposed in such a way that when hollow member 19 is pushed fully inward, see lower half of FIG. 2, catch 25 with catch pin 26 can farther engage the longitudinal slot at the back, further inside end thereof when catch 25 is activated via operating pin 27 protruding outward through housing 2. Pin 27 can also be used to release catch 25 again, thereby releasing probe electrode hollow member 19 again for an outward motion due to the spring force (spring 23).

Diametrically opposite catch 25 is switch 28 for the laser function. Switch 28 is operated with the help of resilient, lamellar switch lever 29 which engages the other, opposite longitudinal slot of probe electrode hollow member 19, i.e. bearing portion 21 thereof, and which is swiveled toward the back upon the inward shift of hollow member 19 through the front end of the slot on which it comes to rest, thereby operating switch 28.

Via spacing pins, screws or the like not shown in detail, mounting body 13 further carries printed circuit board 30 with the measuring circuit (31; FIG. 6) for the skin resistance measurement, with the circuits for pilot light 7 and optical display device 8 for the skin resistance measurement and with the necessary circuit parts for diode laser 15. The electric connections are omitted in FIG. 2 for clarity's sake, but can be seen in the representation of FIG. 6.

FIG. 6 illustrates the electric circuit of present unit 1 in a very schematic block diagram, showing measuring circuit 31 provided on printed board 30 (see FIG. 2) only very generally by a block. Skin resistance measuring circuit 31 is electrically connected at its input via resistor 32 with the probe electrode, i.e. with conical test prod 4, and it drives LED row optical display device 8 in accordance with the skin resistance measured, more or fewer diodes of this LED row being illuminated depending on the skin resistance measured. The sensitivity of measuring circuit 31 can be adjusted as mentioned via sensitivity switch 6, which is preferably an adjusting rheostat, e.g. an adjusting potentiometer with three positions.

The counterelectrode for the skin resistance measurement is formed by electroconductive housing 2, which is illustrated only very schematically by a block in the circuit diagram of FIG. 6. FIG. 6 further shows battery block 10, which is constructed for example of four 1.5 volt cells (one can also use rechargeable accumulator cells), and operating switch 5 formed by a pushbutton. Switch 28 is formed as a reversing or single-pole double throw switch, as recognizable from FIG. 6. Switch 28 is located normally in the position shown in FIG. 6, in which measuring circuit 31 is connected to battery block 10 (provided operating switch 5 is pressed) to perform the skin resistance measurement. As mentioned, switch 28 is operated mechanically by the probe electrode, i.e. test prod 4, when it is pushed back via switch lever 29 (see FIG. 2), measuring circuit 31 then being separated from battery block 10 and laser unit 15 connected to battery block 10. In parallel to laser unit 15, pilot light 7 for laser 15 formed by an LED is thereby made alive via series resistor 33.

The laser circuit with laser unit 15 and the corresponding pilot light switching branch is referred to very generally as 34 in FIG. 6, whereas the skin resistance measuring device with the probe electrode or test prod 4 and actual measuring circuit 31 is designated as 35. Measuring circuit 31 and laser unit 15 can be constructed in conventional fashion, for example in principle as disclosed in the abovementioned prints, so that further explanation thereof can be omitted. In particular measuring circuit 31 can be constructed with an operational amplifier not illustrated in detail, and laser unit 15 can be a commercially available diode laser unit, for example of laser class 3a, with a restriction of the laser power to 3 mW and with a wavelength of 670 nm.

In operation, as illustrated generally in FIG. 1, a skin area e.g. is scanned with test prod 4—pressed in somewhat against the spring force—of unit 1 held in one hand to elicit the desired acupuncture point by skin resistance measurement. When a maximum is displayed on optical display device 8 the desired acupuncture point is localized, and unit 1 is no longer moved further over the skin area but pressed firmly onto the skin at this localized site, so that probe electrode hollow member 19 is pushed inward up to the stop, thereby operating switch (reversing switch) 28 to switch off skin resistance measuring device 35 and switch on laser unit 15. One must of course thereby hold down operating switch 5.

If a so-called "laser shower" is desired, catch 25 can be operated via pin 27 in the fully pushed-in position of probe electrode hollow member 19, so that laser unit 15 is put in continuous operation (instead of the previously described "touch-key operation") in which unit 1 can be lifted off the skin area to be treated without interrupting laser beam 20.

The invention was explained above with reference to especially preferred embodiments, but modifications and variations are of course possible within the scope of the invention. For example it is conceivable to use, instead of described housing 2 with a square cross section as illustrated in FIGS. 4 and 5, a cylindrical housing with a circular or elliptical cross section, accordingly adapting mounting body 13 and the arrangement of the corresponding switches and display elements. It is also basically conceivable to use an on-off switch with two fixed positions for operating switch 5 instead of a pushbutton since switch 28, being a safety switch, normally keeps laser unit 15 separated from the voltage unit, i.e. from battery block 10. With regard to the locking function with the help of catch 25 described it is preferable to design operating switch 5 as a pushbutton, however, since when test prod 4 is locked laser unit 15 could otherwise be activated continuously by mistake.

What is claimed is:

1. An apparatus for locating an acupuncture point by measuring characteristics of skin and for performing acupuncture and biostimulation, comprising:

an elongate housing comprising a counter electrode;

a substantially conical test electrode tapering from the housing to an end portion of reduced diameter and having in the interior thereof a tapered channel terminating in an aperture in the end portion to form an annular electrode surface;

a source of laser light for selectively sending a beam of light through the channel; and a lens intermediate the source of laser light and the test electrode for focusing the beam of light in a plane coinciding with the annular electrode surface.

2. The apparatus of claim 1, wherein the aperture has a diameter of about 1 mm.

3. The apparatus of claim 1, wherein the source of laser light is a class 3a laser diode.

4. The apparatus of claim 1, wherein the source of laser light is mounted in the housing for selective movement relative to the lens.

5. The apparatus of claim 1, wherein the lens has a short focal length.

6. The apparatus of claim 1, further comprising a circuit connected to the test electrode for measuring the skin characteristics and for generating a signal representative thereof.

7. The apparatus of claim 6, wherein the circuit measures the resistance of the skin.

8. The apparatus of claim 7, further comprising means for rendering the signal perceptible.

9. The apparatus of claims 8, wherein the means for rendering the signal perceptible is a plurality of laser diodes.

10. The apparatus of claim 6, wherein the test electrode is mounted for telescoping movement between first and second positions relative to the housing.

11. The apparatus of claim 10, wherein the test electrode is resiliently biased into the first position.

12. The apparatus of claim 10, further comprising a first switch actuable in response to movement of the test electrode from the first towards the second position for selectively energizing the circuit for measuring the skin characteristics.

13. The apparatus of claim 12, further comprising a second switch actuable in response to movement of the test electrode into the second position for selectively energizing the source of laser light.

14. The apparatus of claim 13, further comprising a third switch actuable independently of movement of the test electrode and connected in series with the first and second switches.

15. The apparatus of claim 13, wherein the first switch deenergizes the circuit in response to the second switch energizing the source of laser light.

16. The apparatus of claim 13, further comprising selectively releasable means for arresting the test electrode in the second position.

* * * * *

UNITED STATES PATENT AND TRADEMARK OFFICE
CERTIFICATE OF CORRECTION

PATENT NO. : 6,306,160 B1
DATED : October 23, 2001
INVENTOR(S) : J. Leopold Nidetzky Page 1 of 1

It is certified that error appears in the above-identified patent and that said Letters Patent is hereby corrected as shown below:

<u>Title page,</u>
Item [73], Assignee, -- Myles Limited, Douglas, Isle of Man --

Signed and Sealed this

Nineteenth Day of March, 2002

Attest:

Attesting Officer

JAMES E. ROGAN
*Director of the United States Patent and Trademark Office*